United States Patent [19]

Boom et al.

[11] Patent Number: 5,234,809

[45] Date of Patent: Aug. 10, 1993

[54] PROCESS FOR ISOLATING NUCLEIC ACID

[75] Inventors: Willem R. Boom, Amsterdam; Henriëtte M. A. Adriaanse, Arnhem; Tim Kievits, The Hague; Peter F. Lens, Amsterdam, all of Netherlands

[73] Assignee: Akzo N.V., Arnhem, Netherlands

[21] Appl. No.: 728,007

[22] Filed: Jul. 1, 1991

Related U.S. Application Data

[63] Continuation of Ser. No. 496,735, Mar. 21, 1990, abandoned.

[30] Foreign Application Priority Data

Mar. 23, 1989 [NL] Netherlands ................. 8900725

[51] Int. Cl.$^5$ ............................................... C12Q 1/68
[52] U.S. Cl. ........................................ 435/91; 435/6; 422/61; 536/25.4
[58] Field of Search ................. 435/6, 91; 422/61; 536/27

[56] References Cited

U.S. PATENT DOCUMENTS 4,483,920 11/1984 Gillespie et al. ................... 435/6

OTHER PUBLICATIONS

Cox et al. A Single step procedure for the isolation of individual mRNA species from crude lysates of *P. polycephalum*, FEBS Letters, vol. 155, #1, May 1983.

Krawety et al. Isolation & Fractionation of total nucleic acids from tissues & cells, J. of Biochem. Biophys. Methods 1986 12/1-2 (29-36) (abstract only).

M. A. Marko et al., "A Procedure for the large-scale isolation of highly purified plasmid DNA using Alkaline extraction and binding to glass powder", Anal. Bio., 121, pp. 382-387 (1987), USA.

Rikaken, K. K., "Glass Particles for recovery of DNA", Chemical Abstracts, vol. 102, 1985, No. 200711-u, USA.

J. Xuan et al., "Recovery of DNA for agarose gel using glass powder adsorption method and its application to the isolation of yeast plasmids" Chemical Abstracts, vol. 101, No. 187466a, 1984, USA.

*Primary Examiner*—Christine M. Nucker
*Assistant Examiner*—Jeffrey Stucker
*Attorney, Agent, or Firm*—Donna Bobrowicz; William M. Blackstone

[57] ABSTRACT

The invention relates to a process, a combination of means for isolating nucleic acid from a nucleic acid-containing starting material and a testkit in order to amplify the nucleic acid obtained by said process. More in particular, the invention relates to a process and a kit for isolating nucleic acid from a nucleic acid-containing biological material such as whole blood, blood serum, urine, feces, cell cultures and the like.

14 Claims, No Drawings

PROCESS FOR ISOLATING NUCLEIC ACID

This is a continuation of application Ser. No. 07/496,735 filed Mar. 21, 1990, abandoned.

The invention relates both to a process and a combination of means for isolating nucleic acid from a nucleic acid-containing starting material as well as a testkit in order to amplify the nucleic acid obtained by said process. More in particular, the invention relates to a process and a kit for isolating nucleic acid from a nucleic acid-containing biological material, such as whole blood, blood serum, buffy coat (the crusta phlogistica or leukocyte fraction of blood), urine, feces, liquor cerebrospinalis, sperm, saliva, tissues, cell cultures and the like. Nucleic acid as isolated from above-mentioned biological material can also comprise the endogenous nucleic acid from the organism from which the sample is derived and any foreign (viral, fungal, bacterial or parasitic) nucleic acid.

Known methods of isolating nucleic acid (NA) from complex starting materials like whole blood, blood serum, urine or feces usually comprise lysis of biological material by a detergent in the presence of protein degrading enzymes, followed by several extractions with organic solvents, e.g., phenol and/or chloroform, ethanol precipitation and dialysis of the nucleic acids. These known methods of, e.g., isolating (double-stranded) DNA from clinical material are very laborious and time-consuming. The relatively large number of steps required to purify NA from such starting materials increase the risk of transmission of NA from sample to sample in the simultaneous processing of several clinical samples. When the NA is isolated for the subsequent detection of the presence of NA of, e.g., a pathogen (e.g., a virus or a bacterium) by means of a nucleic acid amplification method for example the utmost sensitive polymerase-chain-reaction (PCR, Saiki et al, Science 230, 1985, 1350), the increased risk of such a transmission of NA between different samples which causes false positive results is a serious drawback.

An example of such a known method sensitive to contamination is the procedure described in Analytical Biochemistry 162, 1987, 156 for isolating total RNA from tissues and cell cultures. According to this method the RNA is subjected to a single extraction with an acid guanidinium thiocyanate-phenol-chloroform mixture from the biological starting material. After phase separation the RNA can be recovered in useful condition within 4 hours by further processing the aqueous phase.

In Analytical Biochemistry 162, 1987, 463, there is described a procedure for isolating DNA from tissues and cell lines, in which the cells are dispersed in a guanidine hydrochloride-containing buffer and ethanol precipitated. With this known method sensitive to contamination a useful NA product can also be isolated within a few hours after further processing the separated DNA.

These known procedures, however, cannot be used successfully in complex starting materials, e.g., whole blood and blood serum.

It is an object of the invention to provide a process which removes the drawbacks of the known processes.

More in particular, it is an object of the invention to provide a process with which nucleic acid (i.e. DNA and/or RNA) can be isolated immediately (without pretreatments) from complex starting materials, such as different types of biological materials, in an unprecedentedly rapid, simple and reproducible manner in such undamaged conditions and high purity that it can then be used as a reagent in molecular biological reactions.

It is a further object of the invention to provide a process which differs from the known processes by a low risk of contamination as compared with other samples and persons, i.e. enables simultaneous processing of several clinical samples at a minimum risk of transmission of NA between different samples, and also means a lowest possible risk of contagion of persons by viruses or bacteria that may be present in the samples to be processed.

These objects are realized according to the invention by a process for isolating nucleic acid from a nucleic acid-containing starting material, characterized by mixing the starting material, characterized by mixing the starting material with a chaotropic substance and a nucleic acid binding solid phase, separating the solid phase with the nucleic acid bound thereto from the liquid, whereafter thus obtained solid phase-nucleic acid complexes were washed, and if required the nucleic acid was eluted from said complexes.

Although in a wide sense the invention is applicable to any nucleic acid-containing starting material, including foods and allied products, vaccines and milk infected with a virus or a bacterium, the invention is particularly applicable to a process in which the starting material employed is a nucleic acid-containing biological material, such as whole blood, blood serum, buffy coat, urine, feces, liquor cerebrospinalis, sperm, saliva, tissues and cell cultures (such as mammalian cell cultures and bacterial cultures). Of course, the process according to the invention is also applicable to relatively pure input materials, such as the product of a PCR or the product to be purified further of another process for recovering nucleic acids. However, some types of nucleic acid-containing biological materials, such as vegetable material, some gram-positive bacteria and some yeasts and moulds, cannot immediately function as an input material in the process according to the present invention, because owing to their special cell wall structure they do not lyse into a chaotropic substance. Therefore, such starting materials require a pretreatment rendering the cells accessible, e.g., a preceding cell lysis, after which the resulting lysate can be subjected to the process according to the invention.

By nucleic acid (NA) is meant both DNA and RNA, both in any possible configuration, i.e. in the form of double-stranded (DS) nucleic acid, or in the form of single-stranded (ss) nucleic acid, or as a combination thereof (in part ds or ss).

Essential according to the invention in the use of a nucleic acid binding solid phase e.g. silica particles capable of binding the NA in the presence of a chaotropic substance. By silica are meant $SiO_2$ crystals and other forms of silicon oxide, such skeletons of diatoms built up from $SiO_2$, amorphous silicon oxide and glass powder. Also alkylsilica, aluminum silicate (zeolite), activated silica with $-NH_2$, latex particles, certain polymeric materials forming the inside wall of a cuvette or a microtiter plate, or filter materials for example consisting of nitrocellulose are suitable as nucleic acid binding solid phase according to the invention.

For the matter using silica particles, it was known from PNAS 76, 1979, 615, that dsDDNA in a highly concentrated solution of chaotropic salt NaI (sodium iodide) can be released from agarose and can be bound to glass. This publication describes two procedures for isolating DNA from an agarose gel, both of which use in a first step an NaI solution to dissolve the agarose. In one procedure the DNA is precipitated in a second step with acetone, while according to the other procedure the DNA is bound in a second step to glass particles and is then eluted into an aqueous buffer. This method, however, is of no use to more complex starting materials, such as body fluids and other biological starting materials. In this article there is also no disclosure for an one-step procedure according to the invention.

It is recommendable according to the invention to use silica particles having a suitably selected particle size so that a high degree of purity of the bound and then eluted nucleic acid is immediately obtained from an impure starting material.

A preferred embodiment of the invention is characterized by using silica particles having a practical size ranging substantially between 0.05 and 500 μm. By the term "substantially" is meant that 80% or more, preferably more than 90%, of the silica particles are within the particle size range defined. In order to ensure easy processing of the bound NA, it is preferred that the silica particles employed have a particle size range substantially between 0.1 and 200 μm, while a process in which the silica particles employed have a particle size ranging substantially between 1 and 200 μm is most preferred. It is true that the NA-binding capacity of the silica particles is higher as the particles are smaller, but especially in the case of an NA-rich input material and in the case of relatively long NA molecules the use of extremely small silica particles will result in that the NA-silica complexes formed cannot be efficiently redispersed anymore. This means that the bound NA cannot be recovered from the complexes in a pure form. When human blood is used as an input material, this problem sometimes occurs if there is used a non-fractionated silica having particle sizes within the range of 0.2–10 μm. The formation of aggregates that cannot be redispersed anymore may be avoided by using a fractionated silica, the particle size of which is within the range of 1–10 μm. When an input material rich in cells is used, such as bacterial cultures, it is found, however, that the use of such a coarse silica fraction is not sufficient to avoid the formation of hardly redispersible aggregates and optimum results are obtained if there is used an even coarser silica, such as a diatomaceous earth having particle sizes within the range of 2–200 μm.

In another preferred embodiment the NA binding solid phase is in the form of a filter or even forms part of the vessel in which the sample with chaotropic substance is contained. The latter forms for the NA binding solid phase eliminates the necessity of centrifugation or filtration for further sample processing and NA isolation.

According to the invention it is essential to use a chaotropic substance in addition to the above-mentioned nucleic acid binding solid phase such as silica particles. By chaotropic substance is meant any substance capable of altering the secondary, tertiary and/or quaternary structure of proteins and nucleic acids, but leaving at least the primary structure intact. Examples thereof are guanidinium (iso)thiocyanate and guanidine hydrochloride. Also sodium iodide, potassium iodide, sodium (iso)thiocyanate, urea or mutual combinations therewith are very suitable in combination with nucleic acid binding solid phases for the isolation of NA from a nucleic acid-containing starting material. According to the invention the chaotropic quanidium salt employed is preferably quanidinium thiocyanate (GuSCN).

The process according to the invention will usually be carried out in such a way that the starting material is mixed with sufficiently large amounts of chaotropic substance for instance guanidinium salt and for instance silica particles to release essentially all of the nucleic acid present in the starting material and bind it to said silica particles. A suitable protocol is, e.g., the addition of a suspension of silica particles to a buffered GuSCN solution present in a reaction vessel, followed by addition of the sample and thoroughly mixing. Then there will take place lysis of cells and optionally present viruses, and releasing NA will be bound to the silica particles almost instantaneously. The resulting silica-nucleic acid complexes will then be separated from the liquid, e.g., by rapid sedimentation (centrifugation) and disposal of the supernatant (e.g., by suction), and then the complexes (e.g., in the form of a silica-nucleic acid pellet) will be washed (redispersing or homogenization), e.g., with a chaotropic guanidinium salt-containing washing buffer using, e.g., a vortex mixer, and sedimented again. Preferably, the silica-nucleic acid complexes washed with washing buffer are further washed successively with an alcohol-water solution (most preferably about 70% ethanol to restrict losses in yield) and with acetone, followed by drying to remove the acetone (e.g., while heating). Then the NA present in the washed and dried silica-nucleic acid complexes is eluted by means of an aqueous elution buffer. The selection of the elution buffer is co-determined by the contemplated use of the isolated NA. Examples of suitable elution buffers are TE buffer, aqua bidest and PCR buffer (see the part "Materials and Methods"). Preferably, all of these steps are carried out in a single reaction vessel (e.g., a 1.5 ml Eppendorff tube of polypropylene), and the purified NA is recovered in a relatively small volume, e.g., less than 100 μl. The thus isolated NA is free from nucleic acid-degrading enzymes and has such a high purity that it can immediately serve as a substrate for different enzymes, such as DNA polymerases (e.g., Taq-DNA polymerase), DNA restriction enzymes, DNA ligase, and reverse transcriptase (such as AMv reverse transcriptase).

In the process according to the invention, e.g., a sufficient amount of NA can be isolated from 50 μl whole blood, without preceding separation of plasma and cells, in about 45 minutes so as to demonstrate NA sequences by means of an amplification method such as the PCR method or the sd-called NASBA method as described in EP 0329822 (NASBA=nucleic acid sequence based amplification). The invention however, is also applicable to various other biological materials containing NA, such as serum, feces, urine, etc. For this reason the invention is useful in the diagnostics of bacterial and viral infections, as well as in a study of gene polymorphisms within the scope of the prenatal diagnostics and the diagnostics of predisposition to hereditary tumours.

In the method of NA isolation according to the invention the risk of contamination is very low, because the whole procedure can be carried out in a single reaction vessel and the NA released from the crude starting material in the first step of the process is at least largely bound to the solid phase during the whole further purification procedure. The risks for personnel, inherent to the processing of material possibly infected with viruses or bacteria, remain limited essentially to the first step of the isolation procedure in which the sample is placed in the reaction vessel. In this first treatment the potentially present pathogens are efficiently inactivated. The process requires no special peripheral equipment (a vortex mixer, a centrifuge of the 12.000 g Eppendorff type and a waterbath or Eppendorff heating block belong to the standard laboratory equipment) and no specialist biochemical knowledge, so that the process is very suitable for routine NA isolation from large numbers of samples in other words for automation. By the process according to the invention more than 10 and even 24 or more different samples can be processed in about 1 hour.

The invention not only relates to a process but also to a combination of means for isolating nucleic acid from a nucleic acid-containing starting material and a testkit in order to amplify the nucleic acid obtained by said process.

In an embodiment a combination of means according to the invention comprises (a) a guanidinium (iso)thiocyanate-containing lysis buffer, (b) an aqueous suspension of silica particles having a particle size ranging substantially between 0.05 and 500 μm, preferably between 0.1 and 200 μm and most preferably between 1 and 200 μm, (c) a guanidinium (iso)thiocyanate-containing washing buffer, and if required (d) an elution buffer.

Thus a combination of means according to the invention may be composed of, e.g., the following 4 components:

component 1: a buffered guanidinium (iso)thiocyanate solution;
component 2: a suspension of silica particles;
component 3: a washing buffer: and (optionally)
component 4: an elution buffer.

If required, components 1 and 2 could be combined, which, however, leads to a limited shelf life.

Other reagents that are preferably used in the method of NA isolation according to the invention, such as ethanol and acetone, belong to the standard laboratory equipment.

The invention will now be illustrated by a number of examples. In the preceding part the employed materials and methods will be described.

MATERIALS AND METHODS

A) Suspension of Silica Coarse (SC)

Use was made of silicon dioxide ($SiO_2$), supplied by Sigma, having a particle size distribution of 0.5-10 μm, 80% of which ranged between 1 and 5 μm.

60 g silica were suspended in aqua bidest (up to a volume of 500 ml) in a cylinder having a diameter of 5 cm; the height of the aqueous column was 27.5 cm. After 1× g sedimentation for 25 hrs at room temperature supernatant was sucked off, until 70 ml were left. Aqua bidest was added up to 500 ml, and the particles were resuspended by shaking the cylinder. After 1× g sedimentation for 5 hrs supernatant was sucked off, until 60 ml were left. After addition of 600 μl 32% (w/v) HCl the particles were resuspended by vortexing. The suspension was made up in aliquots of 4 ml in 6 ml bottles, which were tightly closed and heated in an autoclave at 121° C. for 20 min. This sedimentation protocol led to an enrichment of the larger silica particles, i.e. the particles having a particle size above 1 μm, as was established by an electron-microscopic examination. Moreover, the autoclave treatment of an acid (pH about 2) silica suspension results in that optionally present nucleic acid is fully degraded. The thus obtained suspension of Silica Coarse will hereinbelow be referred to as SC.

Suspensions of Silica derivatives

Silica was derivatized with methylacrylamide silicondioxide having alkyl-tails with a length of 2 to 18 C-atoms. The size of the derivatized silica particles varied from 63 to 200 μM. The pore size of the particles used was 500 Å. These silica derivates (12 $MAAMC_2-C_{18}$) were supplied by Diosynth, Oss.

For the NA isolation (example H1) 0.5 g of the derivatized silica particles were suspended in 1 ml aqua bidest. These silica suspensions were pretreated with 120 μl 32% (w/v) HCl for 30 min. at 90° C.

Suspensions of polystyrene latex particles

Use was made of two types of polystyrene latex particles. The polystyrene latex VQ69 red had been absorbed with sodium-dodecylsuccinate sulfate groups and has a particle size of 424 nm. The polystyrene latex VQ58B had a smaller size (328 nm) and no sulfate group has been absorbed on the outside.

Use was made of three, hydrophilic, glycidylmethacrylaat polystyrene latex particles. The size of AGF27G; ACN3 red and AGYI515 were 933 nm, 206 nm and 846 nm respectively. All the mentioned polystyrene particles were supplied by ARLA-Arnhem.

Commercial filters

Use was made of
1. PVDF an Immobilon Transfer Membrane (hydrophobic) supplied by Millipore.
2. Nitrocellulose supplied by Schleicher and Schuell (0,2 μM Ref.no.401.396).
3. Hybond-N a Nylon Hybridization membrane (0,45 micron, lot: 16872) supplied by Amersham.

B) L2 buffer

L2 buffer (0,1 M Tris.Cl pH 6.4) was prepared by dissolving 12.1 g TRIS (Boehringer) in 800 ml aqua bidest., adding 8.1 ml 37% (w/v) HCl and bringing the volume to 1 litre with aqua bidest.

C) Washing liquid L2

The washing liquid L2 was prepared by dissolving 120 g GuSCN (guanidine thiocyanate of Fluka) in 100 ml L2 buffer.

Washing liquids L2*

The washing liquid L2* was prepared by dissolving 2.45 q KI (potassium iodide from Merck) in 25 ml L2-buffer.

For preparing a NaI based chaotropic substance, 11.25 g NaI (sodium iodide from Merck) was dissolved in 25 ml L2-buffer. For a sodium thiocyanate based chaotropic substance, 6.1 g NaSCN (Baker) was dissolved in 25 ml L2-buffer.

For preparing a chaotropic substance containing KI and urea (8M) 12.45 q KI and 12.0 q urea were dissolved in L2-buffer (25 ml). Similarly chaotropic substances combining urea with NaI and urea with NaSCN were prepared.

D) Lysis buffer L5

The lysis buffer L5 was prepared from 100 ml L2 buffer by dissolving therein 120 g GuSCN (gently shaking in a warm water bath of about 60° C.), then adding 26.0 g of 40% (w/v) Dextran sulfate (Pharmacia LKB)

solution, 22 ml of 0.2 M EDTA pH 8, and 2.6 g Triton X-100 (Packard), and then homogenizing the solution. The 0.2 M EDTA pH 8 solution was prepared by dissolving 37.2 EDTA (Titriplex of Merck) and 4.4 g NaoH (Merck) in 500 ml water.

E) Lysis buffer L6

The lysis buffer L6 was prepared from 100 ml L2 buffer by dissolving therein 120 g GuSCN (gently shaking in a water bath of 60° C.), then adding 22 ml of 0.2 M EDTA pH 8, and 2.6 g Triton X-100 (Packard) and then homogenizing the solution.

Lysis buffer L6*

The lysis buffer L6* was prepared from 25 ml L2-buffer by dissolving therein 12.45 g KI (potassium iodide, Merck) (gently shaking in waterbath of 40° C.) subsequently adding 5.5 ml of 0.2 M EDTA (pH 8.0) and 0.65 g Triton X-100 (Boehringer 789704) and finally homogenizing the solution. The same procedure was applied for lysisbuffer L6* with NaI (sodium iodide, Merck) and lysisbuffer L6* with NaSCN (sodium thiocyanate, Baker).

The lysisbuffer L6* with combination KI and urea was prepared from 25 ml L2-buffer by dissolving therein 12.45 g KI (potassium iodide, Merck) and 12.0 g urea (Gibco BRL). Subsequently 5.5 ml of 0.2 M EDTA (pH 8.0) and 0.65 g Triton X-100 (Boehringer) were added and the mixture was homogenized. The same method was followed for the preparation of NaI/urea and NaSCN/urea.

F) Lysis buffer GEDTA

By GEDTA is meant a solution of I20 g GuSCN in 100 ml 0.2 M EDTA pH 8.

G) TE buffer

A buffer suitable for elution is a 10 mM Tris.Cl, 1 mM EDTA solution with pH 7.5 (TE buffer), if desired comprising 0.5 U/$\mu$l RNAsin (Promega).

H) Test tubes

The test tubes were assembled on the same day as the extraction procedure by adding 900 $\mu$l lysis buffer and 40 $\mu$l of an NA carrier (latex beads or silica, such as SC, or diatomaceous earth) to Eppendorff centrifugal tubes (type 3810, 1.5 ml).

I) Washing procedure

A pellet is washed by adding 1 ml washing liquid, then vortexing until the pellet is resuspended, centrifuging for 15 sec. at 1200033 q, and discarding the supernatant by suction.

J) Elution procedure

The elution takes place by adding at least 25 $\mu$l, preferably at least 40 $\mu$l elution buffer, vortexing briefly (2 sec) and incubating for 10 min. at 56° C.

K) Protocol B

This protocol is suitable for isolating dsDNA from complex starting materials, such as human serum, whole blood, watery feces or urine and makes use of Eppendorff test tubes with 900 $\mu$l GEDTA and 40 $\mu$l SC.
1. Vortex test tube until pellet is resuspended.
2. Add 50 $\mu$l starting material (e.g., serum, whole blood, feces or urine) and vortex immediately until homogeneous (5-10 sec.).
3. Leave at room temperature for 10 min. and vortex 5 sec.
4. Centrifuge for 15 sec. at 12000× g and discard supernatant by suction.
5. Wash pellet once with GEDTA.
6. Wash pellet twice with 70% ethanol.
7. Wash pellet once with acetone.
8. Dry pellet for 10 min. at 56° C. with open lid.
9. Elute DNA with 50 $\mu$l TE buffer without RNAsin.
10. Centrifuge for 2 min. at 12000× g; supernatant contains DNA.

L. Protocol Y

This protocol is suitable for isolating NA (simultaneous purification of dsDNA, ssDNA, dsRNA and ssRNA) from complex starting materials, such as human serum, whole blood, watery feces or urine and makes use of Eppendorff test tubes with 900 $\mu$l L6 and 40 $\mu$l SC.
1. Vortex test tube until pellet is resuspended.
2. Add 50 $\mu$l starting material (serum, whole blood, feces or urine) and vortex immediately until homogeneous (about 5 sec.).
3. Leave at room temperature for 10 min. and vortex 5 sec.
4. Centrifuge for 15 sec. at 12000× g and discard supernatant by suction.
5. Wash pellet twice with L2.
6. Wash pellet twice with 70% ethanol.
7. Wash pellet once with acetone.
8. Dry pellet for 10 min. at 56° C. with open lid.
9. Elute NA with 50 $\mu$l TE buffer, optionally in the presence of RNAsin.
10. Centrifuge for 2 min. at 12000× g; supernatant contains NA.

Protocol Y*

This protocol is suitable for isolating NA from complex starting materials, such as human serum, urine or bacterial cultures.

Procedure

Eppendorff tubes were used with 900 $\mu$l L6* and 40 $\mu$l SC.
1. Vortex test tube until pellet is resuspended.
2. Add 50 $\mu$l starting material (serum-plasmid, urine-plasmid mixtures or overnight bacterial culture) and vortex immediately until homogeneous (5 sec.).
3. Leave at roomtemperature for 10 min. while mixing.
4. Centrifuge for 15 sec. at 14.000 g discard supernatant by suction.
5. Wash pellet twice with L2* washing liquid.
6. Wash pellet twice with 70% ethanol.
7. Wash pellet once with acetone.
8. Dry pellet for 10 min. at 56° C. with open lid.
9. Elute NA with 50 $\mu$l TE-buffer (10 mM Tris-1 mM EDTA pH
10. Centrifuge for 2 min at 14.000 g; supernatant contains NA.

Protocol Y**

This protocol is suitable for isolating NA in presence of GuSCN as chaotropic substance and a filter capable of binding NA (see Materials & Methods). The NA detection was performed by polymerase chain reaction by bringing this filter directly in the polymerase chain reaction mix, thus without prior elution of the NA from the filter.

Procedure

Eppendorff tubes were used with 900 µl L6 lysis buffer and a filter (size 1 cm/1 cm)
1. Add 50 µl nucleic acid containing solution and vortex the test tube briefly.
2. Leave at roomtemperature for 10 min. while mixing.
3. Discard supernatant.
4. Wash filter twice with L2 washing liquid.
5. Wash filter twice with 70% ethanol.
6. Dry filter 10 min. at 56° C. with open lid.
7. A small piece of the filter was directly added to the polymerase chain reaction solution.

M) Protocol Z

This protocol is suitable for isolating NA from complex starting materials, such as human serum, whole blood, watery feces or urine and makes use of Eppendorff test tubes with 900 µl L5 and 40 µl SC. The isolated NA can be used for hybridization reactions but is less suitable as a substrate for restriction enzymes. T4 DNA ligase, however, is active. As compared with protocol Y, this protocol Z leads to higher NA yield.
1. Vortex test tubes until pellet is resuspended.
2. Add 50 µl starting material (serum, whole blood, feces or urine) and vortex immediately until homogeneous (about 5 sec.).
3. Leave at room temperature for 10 min. and vortex 5 sec.
4. Centrifuge for 15 sec. at 12000× g and discard supernatant by suction.
5. Wash pellet twice with L2.
6. Wash pellet twice with 70% ethanol.
7. Wash pellet once with acetone.
8. Dry pellet for 10 min. at 56° C. with open lid.
9. Elute NA with 50 µl TE buffer, optionally in the presence of RNAsin.
10. Centrifuge for 2 min. at 12000× g; supernatant contains NA.

N) Starting materials

The examples are divided into sections as follows, inter alia (sections A-D) in accordance with the nature of the starting material:
section A: human serum
section B: human whole blood
section C: human urine These sections A, B and C are especially meant to show that both dsDNA and ssRNA can be isolated in pure form.
section D: human feces This section D shows, among others, that the dsRNA can also be isolated.
section E: single stranded DNA This section E comprises experiments showing that the invention can be used for isolating ssDNA.
section F: diatomaceous earth This section F shows that diatom skeletons are very useful as the silica particles to be used according to the invention. It is also shown that the invention can be used for isolating NA from different gram-negative bacteria.

Section G shows that NA can be purified from bacterial cells using various chaotropic substances.

Section H and I show the isolation of DNA with the aid of alternative solid phases.

There was always used an amount of 50 µl. The blood used in section B and F was always fresh blood drawn off in the presence of EDTA to prevent clotting (using the Venoject system of Terumo N.V., Louvain, Belgium, collecting tubes of the type VT-574 TKZ). The starting materials used in the other sections (serum, urine and feces) were frozen. In examples A1, A2, A3, B1, B2, B5, B7 and F1 the serum or blood was from the same subject.

O) Further methods

For gel-electrophoretic examination, part of the eluted amount of NA was loaded on a neutral agarose-gel containing I µg/ml ethidium bromide in the buffer system described by Aaij and Borst (Biochim.Biophys. Acta 269. 1972, 192). Photographs were taken under UV illumination of the gel.

In some experiments a known amount of a purified DNA (input DNA) was added to the clinical sample. In these cases an amount of input DNA corresponding to an extraction efficiency of 100% was also loaded on the same gel.

Bacterial plasmid DNA was purified as described by Ish-Horowicz and Burke (Nucleic Acids Res. 9, 1981, 2989) from *Escherichia Coli* HB101, followed by column chromatography with Sepharose CL 2B (Pharmacia, Inc.) and ethanol precipitation. Bacterial plasmid DNA was purified from *Esscherichia Coli* JM101 (J. Messing, Rec. DNA Techn. Bull. 2:43-48(1979) as described by Birnboim and Doly (Maniatis, T. et al., Molecular Cloning, CSH, New York). The pCMV-E contains a 0.4 kb human cytomegalo virus DNA fragment cloned in the 2 kb vector pHC 624 (Boros in Gene 30, 1984, 257); pEBV-10 contains a 0.9 kb Epstein Barr virus DNA fragment cloned in the same vector. To obtain a plasmid preparation enriched for relaxed circular (CII) molecules, pEBV-10 DNA (2.9 kb) was treated with DNAse I. Component II molecules serve as a model for purification of Hepatitis B viral DNA which is present in virions as a 3.2 kb relaxed circular DNA molecule.

The pGem3p24 contains a 1,45 kb HIV sequence; the construction of pGem3p24 is described below.

The sequence of HIV HxB2 DNA has been described by several authors (J. virol. 61, 633-637(1987); Nature 326, 711-713(1987); Aids Res. Hum. Retrovirus 3, 41-55(1987); Aids Res. Hum. Retrovirus 3, 33-39(1987) and Science 237, 888-893(1987)).

HIV HxB2 DNA was partially cleaved with FokI at sites 1189 and 2613 of the original HIV HxB2 sequence. The nucleotide nrs. refer to the Genebank designation.

The FokI sites of this fragment were filled up using Klenow, DNA polymerase (Maniatis, vide supra) and cloned (Maniatis, vide supra) in the polylinker SmaI-site of plasmid pUC-19. The resulting plasmid which carries the HIV HxB2 DNA fragment was called pUC19-p24.

To obtain plasmid pGem3p24, the 1450 bp EcoRI-BamHI fragment of pUC19-p24 was cloned in the EcoRI-BamHI digested vector pGem3 (2867 bp; Promega Corporation, Madison USA).

The primers used in the PCR method were synthesized on an oligo-synthesizer apparatus (from Applied Biosystem). Nucleotide sequence of the primers ES47 (25 mer) and ES75 (47 mer) are given below.

```
            10         20
ACAGGAGCAG ATGATACAGT ATTAG
```

ES75
```
            10         20         30         40
AATTCTAATA CGACTCACTA TAGGGCCTGG CTTTAATTTT ACTGGTA
```

In most of the RNA isolation experiments (examples A3, B5, B6, B7, C2, D1, E1, F1 and F2) no precautions were taken other than the optional use of RNAsin in the elution buffer to avoid RNA degradation during the purification procedure. Gloves were only worn during the addition of the clinical samples to the test tubes; no RNAse inhibitors were used for the preparation of the reagents; and non-autoclaved Eppendorff vessels and pipette tips were used. Examples F1 and F2, among others, have shown that the presence of RNAsin during elution is not strictly necessary.

The enzymes used were commercially available and were used as recommended by the manufacturer. All restriction enzymes, as well as RNAse A, T4 ligase and AMV reverse transcriptase were from Boehringer (Mannheim). Tao-DNA polymerase was from Cetus Inc. The polymerase chain reactions (PCR) were performed with a Perkin Elmer Cetus DNA-thermal cycler.

For different uses it is of essential importance that the reagents used in the process according to the invention, especially the NA carrier (for instance silica particles) and the lysis and washing buffers containing the chaotropic substance, should not be impurified by nucleic acid (e.g., by NA containing bacteria or viruses). This can be ensured for the NA carrier by heating it in an autoclave for 20 min. at 121° C. However, this method is not useful in the GuSCN-containing lysis and washing buffers (GEDTA, L5, L6, and L2), both by reason of a possible loss of activity and because of the attendant risk for the environment. In order to make these reagents (as much as possible) nucleic acid-free, they may be passed through a column of silica particles in accordance with the invention. Due to the lysing properties of the GuSCN-containing buffers and the property of silica to bind NA in the presence of the chaotropic substance GuSCN, such a procedure leads to an NA-free buffer. The column itself can be made nucleic acid-free by heating for, e.g., one ore more hours at, e.g., 500° C. or more.

P) DNA types

CI:Covalently closed circular DNA (plasmid)
CII:relaxed (nicked) circular DNA (plasmid)
CIII:Linear DNA (linearized plasmid)
LMW:low molecular weight DNA (<0.5 kb); HoaII digest of pHC 624, fragments of 471 bp, 404 bp, 242 bp (2 fragments), 190 bp, 147 bp, 110 bp, 67 bp and some smaller fragments of undetermined lengths.
MMW:medium molecular weight DNA (0.5-29 kb); HindIII digest of phage lambda DNA, fragments of 23 kb, 9.4 kb, 6.7 kb, 4.4 kb, 2.3 kb, 2.0 kb and 0.56 kb.
HMW:high molecular weight DNA (>29 kb).
ssDNA:phage M13mp9 single stranded DNA (Boehringer).

SECTION A

DNA/RNA purification from human serum

In human serum NA can be present, e.g. in viruses or bacteria. These organisms can occur both in free form and also bound in immune complexes. The amounts of NA are usually so low that detection through agarose gel electrophoresis and Uv illumination of ethidium bromide/NA complexes is impossible. To show that DNA can be purified from human serum, microgram quantities of purified DNA were added to the serum, and then the DNA was isolated according to protocol B (examples A1 and A2). To show that DNA and RNA can be simultaneously purified from human serum, cultured mammalian cells or bacteria (carrying a small plasmid) were added to the serum, and then NA was isolated according to protocol Y (Example A3). Finally, example 4 shows that, by protocol Y, RNA present in human serum can be purified from HIV (Human Immunodeficiency virus) and can be detected by the PCR method. Example A5 shows that, by protocol Y*, DNA in human serum can be purified using various chaotropic substances in combination with silica as nucleic acid binding solid phase.

EXAMPLE A1

DNA purification from human serum

Human serum (500 μl) was mixed with known amounts of purified DNA [100 μl LMW (45 μg), 20 μl MMW (20 μg), 40 μl CI/II (20 μg)] and 10 samples of 66 μl were used as input material for 10 DNA extractions according to protocol B. The amount of SC (suspension of Silica Coarse) present in the test tubes was varied in this experiment between 2.5 and 40 μl. The extractions were carried out in duplicate and half (30 μl) of the eluted DNA from each sample was electrophoresed through a 1% agarose gel. For comparison, half of the amount of input DNAs were also loaded on the same gel in control lanes.

Double-stranded DNA, both linear (range 23 kb to approximately 60 bp), covalently closed (CI) and relaxed circular (CII) DNA were efficiently isolated if the amount of SC exceed 10 μ. The yield of the largest MMW fragment (approx. 23 kb) seems relatively low when compared to the smaller fragments, which in view of other experiments, may be attributed to shearing of high molecular weight fragments.

The control lanes show respectively the amount of LMW, CII/CI and MMW DNA which would be found in an extraction efficiency of 100%. As previously stated, a CII-rich (DNAse I-treated) 3 kb plasmid (pEBV-10) was used as input material.

EXAMPLE A2

DNA isolated from human serum is a good substrate for restriction enzymes and T4 DNA ligase Purified DNA preparations were added to 12 human serum samples of 50 μl. DNA was isolated from these 12 mixtures according to protocol B; elution was effected with 50 μl TE. Half of the eluted DNA was treated (in duplicate) either with one of the following three restriction enzymes: EcoRI, BamHI and BolII (these are active in low-salt, medium-salt and high-salt buffers, respectively), or treated with T4 DNA ligase, or not treated. The DNA samples were electrophoresed through a 1% agarose gel and visualized by Uv illumination.

The results of the T4 ligase treatment (1 h at 37° C., 3 units of T4 ligase in a 30 μl reaction volume) shows a shift in molecular weight of the DNA fragments and indicates that the DNA isolated from human serum is not significantly affected by exonucleolytic degradation.

The results for 8 serum samples to which a purified plasmid (pCMV-E; 3.3 μg; 1.5 μl) was added shows respectively that for EcoRI, BamHI and BqlII digests all restriction enzymes linearized the plasmid. All restriction enzyme incubations were done in a 30 μl reaction volume for 1 h at 37° C. with 9 units of enzyme.

EXAMPLE a3

Simultaneous isolation of DNA and ssRNA from a human serum

Since in human serum only very low levels of RNA are present (e.g., in viruses, bacteria or cells) which are not detectable by Uv illumination of ethidium-bromide stained gels, exogenous RNA sources were added to human serum samples. Mammalian cells or bacteria were used as exogenous RNA sources. The NA was isolated from the samples according to protocol Y and eluted in 50 μl TE with 0.5 U RNAsin per μl in the absence or in the presence of RNAseA (40 ng per μl of the elution buffer). The results of the subsequent electrophoresis through a 1% agarose gel shows that RNA and DNA can be detected. The mammalian cells added were per 50 μl serum sample $5 \times 10^5$ rat 10B cells (Boom et al., J. Gen. virol. 69, 1988, 1179) while the bacteria added were per 50 μl serum the cell pellet of a 100 μl overnight culture of the *E. coli* strain HB101 containing the plasmid pCMV-E.

EXAMPLE A4

Polymerase chain reaction for the detection of Human Immunodeficiency virus RNA isolated from human serum NA (75 μl) was isolated from 2 human serum samples of 50 μl each (patients F and H) according to protocol Y. The serum of patient F contained a high (2700 pg/ml) level of the HIv antigen P24 (according to the HIV P24 antigen solid phase immunoassay of Abbott Laboratories) but was negative for HIV antibodies (according to the HIV antibodies ELISA of Abbott Laboratories), and the serum of patient H was negative in both tests.

Part of the isolated NA (43 μl) was treated with RNAse-free DNAse (Boehringer; 1 U DNAse/μl) for 90 min at 37° C. After ethanol precipitation and heat inactivation for 15 min at 68° C., the RNA was suspended in 15 μl TE buffer. A 5 μl portion of this RNA preparation was either or not treated with 0.4 U/μl AMV reverse transcriptase (30 min at 42° C.; reaction volume 20 μl) in the presence of HIV specific primers. Then the reaction volume was made up to 100 μl by adding 80 μl of 1.25 x concentrated PCR buffer including dNTPs, 1 U of Taq-DNA polymerase was added, and the amplification was started (1 cycle comprised 1 min at 95° C., min at 55° C., 2 min at 2° C.). 10 μl aliquots were taken from the reaction mixtures at 20, 25, 30 and 35 cycles and were applied to a 2% agarose gel. The expected 330 bp HIV amplimer fragment was already observed after 25 cycles for patient F RNA that had been treated with reverse transcriptase, suggesting that HIV RNA was present in his serum.

EXAMPLE A5

DNA purification with several chaotropic substances

Ten 50μl samples of human serum were mixed with each 10 μg of purified pGem3p24 DNA consisting of CI and CII form (see methods). These 10 plasmid/serum mixtures were used as input material for extractions according to protocol Y* For the concentrations of chaotropic substances used see Table A5.1.

After extraction 25% of the eluted DNA from each sample was analyzed on 0.8% agarose gel. To allow quantitation of plasmid DNA recovery input DNA was also loaded directly on the same gel.

After electrophoresis the gels were photographed under UV illumination and the efficiency of DNA recovery was visually judged on the basis of the plasmid bands intensities (see legend of table A5.1).

Similarly experiments were performed using NaI and NaSCN as chaotropic substances (see sample description below).

TABLE A5.1

Efficiency of recovery of plasmid DNA from human serum samples using various chaotropic substances in combination with silica.

| Sample nr. | chaotropic substance used | Recovery of pGem3p24:CII | Recovery of pGem3p24:CI |
|---|---|---|---|
| 1 | GUSCN | ++ | ± |
| 2 | KI 3M | − | − |
| 3 | KI 3M/urea 1M | − | − |
| 4 | KI 3M/ureum 8M | ++ | + |
| 5 | NaI 3M | − | − |
| 6 | NaI 3M/urea 1M | − | − |
| 7 | NaI 3M/urea 8M | ++ | + |
| 8 | NaSCN 3M | − | − |
| 9 | NaSCN 3M/urea 1M | ± | ± |
| 10 | NaSCN 3M/urea 8M | ++ | + |

Legend:
10 detectable samples prepared as described above and using the chaotropic substances indicated in the table were analyzed.
−: no recovery   ±: little recovery
+: visible recovery   ++: quantative recovery The results summarized in Table A5.1 show that covalently closed (CI) and relaxed circular (CII) pGem3p24 DNA were efficiently isolated when 3M KI, 3M, NaI or 3M NaSCN in combination with 8M urea were used as chaotropic substances. The yield of CII seems relatively high when compared with CI.

SECTION B

DNA/RNA purification from human whole blood

One ml of human blood contains approx. $5 \times 10^9$ erythrocytes which are non-nucleated and do therefore not contribute to the NA amount of blood. The NA amount of blood is largely determined by the white blood cells (approx. $4-10 \times 10^6$ per ml). These cells are embedded in an aqueous medium (plasma) containing large amounts of proteins (approx. 70 mg/ml blood). Thus, whole blood is an extremely unpure source for NA purification. The examples of section B show that notwithstanding NA can be isolated from whole blood by protocols B and Y.

EXAMPLE B1

DNA isolation from human whole blood

Human blood (500 μl) was mixed with known amounts of purified DNA 100μl LMW (45 μg), 80 μl CI/II (40 μg) and 10 samples of 68 μl were used as input material for 10 DNA extractions according to protocol B. In this experiment the amount of SC (suspension of Silica Coarse) present in the test tubes was varied between 2.5 and 40 μl. The extractions were carried out in duplicate and half (30 μl) of the eluted DNA from each sample was electrophoresed through a 1% agarose gel. For comparison, half of the amount of input DNAs was also loaded on the same gel.

Double-stranded DNA, both linear, covalently closed (CI) and relaxed circular (CII) DNA, was efficiently isolated from human whole blood if more than 10 μl SC, were used. The amount of DNA recovered from whole blood was proportional to the amount of SC up to approximately 10 μl. Higher amounts seemed to be saturating.

EXAMPLE B2

DNA isolated from human whole blood is a good substrate for restriction enzymes and T4 DNA ligase Purified DNA preparations were added to 12 human blood samples of 50 μ. The DNA was isolated from these 12 mixtures according to protocol B; elution occurred with 50 μl TE. Half of the eluted DNA was either treated with one of the following three restriction enzymes: EcoRI, BamHI and BqlII (these are active in low-salt, medium-salt and high-salt buffers, respectively), or treated with T4 DNA ligase, or not treated. The DNA samples were electrophoresed through a 1% agarose gel and visualized by UV illumination.

The results of T4 ligase treatment (1 h at 37° C., 3 units of T4 ligase in a 30 μl reaction volume) shows a shift to a higher molecular weight of the DNA fragments and indicates that the DNA isolated from human blood is not significantly affected by exonucleolytic degradation.

The results for 8 blood samples to which a purified plasmid (pCMV-E; 3.3 μg; 1.5 μl) was added show that for EcoRI, BamHI and BglII digests all restriction enzymes linearized the plasmid. All restriction enzyme incubations were done in a 30 μl reaction volume for 1 h at 37° C. with 9 units of enzyme.

EXAMPLE B3

DNA isolation from 10 different samples of blood

In this example 10 different samples of human blood randomly chosen from a blood bank are used as starting material. Of each of the samples the number of white blood cells (WBC) was known. DNA was purified from 50 μl of the samples according to protocol B, and elution occurred with 75 μl TE. One third of the isolated DNA was directly applied to a 1% agarose gel and part (2 μl) of the remainder was used for a PCR.

The same samples were subjected to the same isolation procedure after 3 μl LMW-DNA (6 μg) was added to each 50 μl sample. Here, too, 25 μl of the eluate (75 μl) was directly applied to the gel; another portion of 25 μl of the eluate was first treated with T4 DNA ligase (1 h at 37° C., 2 U in a reaction volume of 30 μl) and then applied to the same gel.

The content of white blood cells (WBC) of blood samples 1-10 was as follows:

| sample No. | WBC $\times 10^9$/l |
| --- | --- |
| 1 | 4.9 |
| 2 | 5.1 |
| 3 | 5.9 |
| 4 | 6.7 |
| 5 | 7.7 |
| 6 | 8.3 |
| 7 | 8.5 |
| 8 | 9.2 |
| 9 | 10.3 |
| 10 | 10.5 |

EXAMPLE B4

Polymerase chain reaction for the detection of the human beta-globin gene in human white blood cells To show that DNA isolated from human whole blood according to protocol B is a good substrate for Taq-DNA polymerase, 2 μl of the DNA isolated from ten different blood samples according to example B3 was subjected to a PCR with beta-globin specific primers. The PCR comprised 32 cycles, each cycle being 1 min at 94° C. and then 3 min at 65° C. part of the amplimers (50%) was electrophoresed through a 2% agarose gel. A 120 bp amplimer and the primer bands could be detected.

EXAMPLE B5

Simultaneous purification of DNA and ssRNA from human blood (reproducibility)

To show that DNA and RNA can be purified from human blood in a reproducible manner, 6 blood samples of each 50 μl from one person were subjected to protocol Y, the NA being eluted in 75 μl TE with RNAsin (0.5 U/μl). A 25 μl portion of the eluate was applied to a neutral 1% agarose gel and electrophoresed. The results show that DNA and RNA can be detected.

EXAMPLE B6

Simultaneous purification of DNA and ssRNA from human blood (10 different samples)

Blood samples of 50 μl from 10 different persons (see example B3) were subjected to protocol Y, the NA being eluted with 40 μl TE with 0.5 U/μl RNAsin. Eluate portions of 3o μl were electrophoresed through a neutral 1% agarose gel. The result shows that both DNA and RNA can be detected.

EXAMPLE B7 simultaneous purification of DNA and ssRNA from human blood

Exogenous RNA sources were added to samples of a human blood. Mammalian cells or bacteria were used as exogenous RNA sources. The NA was isolated from the samples according to protocol Y and eluted in 50 μl TE+0.5 U/μl RNAsin in the absence or in the presence of RNAseA (40 ng per μl of the elution buffer). Per 50 μl blood sample $5 \times 10^5$ rat 10B cells (Boom et al., J.Gen.Virol. 69, 1988, 1179) were added as mammalian cells, and per 50 μl blood the cell pellet of a 100 μl overnight culture of the E.coli strain HB101 containing the plasmid pCMV-E was added as bacteria.

The results show that both mammalian ssRNA (18S and 28S ribosomal RNAs) and bacterial ssRNA (16S and 23S ribosomal RNAs) can be purified from human whole blood.

In addition, genomic DNA and plasmid (form I) DNA are efficiently recovered.

SECTION C

DNA/RNA purification from human urine

In human urine, NA can be present, e.g., in viruses or bacteria and in cells from the urinary tract. The amounts are usually so low that detection through agarose gel electrophoresis and Uv illumination of ethidium bromide/NA complexes is impossible. To show that DNA can be purified from human urine, microgram quantities of purified DNA were added to urine, and the DNA was subsequently isolated according to protocol B (example C1). To show that DNA and RNA can be simultaneously purified from human urine, cultured bacteria (carrying a small plasmid) were added to urine, and the NA was subsequently isolated according to protocol Y (example C2).

Example C3 shows that DNA can be purified from human urine with alternative chaotropic substances such as KI, NaI and NaSCN instead of GuSCN with silica as nucleic acid binding solid phase according to protocol Y*

EXAMPLE C1

DNA purification from human urine

3 $\mu$l LMW DNA (6 $\mu$g) was added to 10 randomly chosen human urine samples of 50 $\mu$l with varying turbidity (samples 4, 5, 6 and 7 were clear, samples 1, 2, 3 and 8 were slightly turbid, and samples 9 and 10 were very turbid). The DNA was isolated according to protocol B and eluted with 75 $\mu$l TE buffer. One third of each eluate was applied to a 1% agarose gel. Another part of 25 $\mu$l was treated with a 1.8 U T4 DNA ligase (1 h at 37° C. in a 30 $\mu$l reaction volume) and applied to the same gel. Marker lanes contain respectively LMW DNA and MMW DNA. The amount of LMW DNA (2 $\mu$g) in a marker lane represents the amount to be observed with an extraction efficiency of 100%.

The results show that DNA can be efficiently purified from human urine with protocol B and is a good substrate for T4 DNA ligase.

The LMW DNA isolated from urine sample No. 10 has been clearly degraded. It was to be expected, however, that naked DNA (as used in this experiment) would be degraded if a urine sample is rich in nucleases. Degradation is therefore likely to have taken place previously during the preparation of the urine/DNA mixtures rather than during purification. The next example (C2) shows that DNA and even ssRNA present in cells (as opposed to naked) can be efficiently recovered from urine sample No. 10.

EXAMPLE C2

Simultaneous purification of DNA and ssRNA from human urine

In this experiment the same 10 urine samples as used in example C1 were mixed with bacteria carrying a 2.4 kb plasmid (pCMv-E). The NA was isolated from these mixtures according to protocol Y and eluted in 75 $\mu$l TE buffer with 0.5 U/$\mu$l RNAsin. One third of the eluate was L electrophoresed through a 1% agarose gel. Another 25 $\mu$l portion of the eluate was treated with 10 U of the restriction enzyme EcoRI which linearizes pCMV-E (1 h at 7° C. in a 30 $\mu$l reaction volume). This treatment was conducted in the presence of 40 ng/$\mu$l RNAseA. The electrophoresis result shows the 23S and 16S ribosomal RNAas as well as the covalently closed (CI) and linear (CIII) forms of plasmid DNA.

EXAMPLE C3

DNA purification with other chaotropic substances

Human urine (50 $\mu$l) was mixed with 400 $\mu$l chaotropic substance, lysis buffer L6* and 1 $\mu$g pGem3p24 DNA. This total suspension was mixed and added to 500 $\mu$l chaotropic substance (see table C3.1) and 40 $\mu$l SiO$_2$ for the purification of DNA according to protocol Y*. The quantity of DNA isolated from urine was analysed using agarose gel electrophoresis. Efficiency of DNA recovery was judged as described in Example A5 and the results are summerized in Table C3.1.

TABLE C3.1

Recovery of plasmid DNA from human urine samples using various chaotropic substances in combination with Silica (see also legends of Table A5.1)

| Sample nr | chaotropic substance used | recovery of pGem3p24 CII | recovery of pGem3p24 CI |
|---|---|---|---|
| 1 | GuSCN/SiO$_2$ | + | + |
| 2 | KI 3M/SiO$_2$ | + | + |
| 3 | NaI 3M/SiO$_2$ | + | + |
| 4 | NaSCN 3M/SiO$_2$ | + | + |

EXAMPLE D1

Purification of rotaviral dsRNA from human feces

Members of the virus family Reovirdae possess a genome consisting of double stranded RNA. Important pathogens belonging to this family are the Rotaviruses which can cause serious diarrhoeas and are then present in vast amounts in feces samples. The rotaviral genome consists of 11 dsRNA segments (see Hishino in J. clin. Microbiol. 21. 1985, 425) which could be isolated from feces supernatant according the protocol B. 100 $\mu$l supernatant obtained by 2 min. centrifugation of the diarrhoea sample at 12000× g were used for the isolation.

The results using samples from 6 different patients with proven rotaviral infection (proven by the Wellcome Rotavirus latex test and by the Kallestad Pathfinder Rotavirus direct antigen detection system) prove that dsRNA can be extracted.

Similar results (usually with higher rotaviral dsRNA yields) were obtained when the first centrifugation step was omitted and the feces samples were directly used as input material for protocol B or Y.

EXAMPLE E1

Purification ssDNA from human blood, serum and urine

To show that single stranded DNA can also be isolated from clinical samples, 1 $\mu$g (4 $\mu$l) of purified phage M13 DNA (M13mp9 DNA, Boehringer) was added to 50 $\mu$l human serum, human blood or human urine and purified according to protocol B or according to protocol Y. All the extractions were carried out in quadruplicate. DNA was eluted in 50 $\mu$l TE buffer, and 25 $\mu$l were electrophoresed through a 1% agarose gel. A marker lane contains 500 ng of M13 ssDNA.

The results show that single stranded DNA can be isolated from human blood, serum or urine by protocol Y and, to a lesser extent, by protocol B.

SECTION F

Binding of NA to diatomaceous earth

Since the skeletons of diatomaceous earths consist almost completely of SiO$_2$, it was examined whether they might serve as the silica to be used. Of each of five different commercially available diatomaceous products [Celatom FW14, Celatom FW50, Celatom FW60, Celite (AK) and Celite 521, Janssen Biochimica, Louvain, Belgium]10 g were mixed with 50 ml aqua bidest and 500 μl 37% HCl, followed by heating the resulting suspensions in an autoclave to 121° C. for 20 min. In examples F1 and F2 the thus obtained suspensions were used for NA extractions according to protocol Y.

EXAMPLE F1

NA isolation from human blood

Human blood was mixed with *E.coli* HB101 bacteria, carrying the plasmid pCMV-E, and the bacterial pellet of 100 μl of an overnight culture were added to 50 μl blood. Samples of 50 μl were used as input material for NA extractions according to protocol Y. Instead of 40 μl SC, 40 μl of the above suspensions of diatomaceous earth were used. The NA was eluted in 75 μl TE buffer, without using RNAse inhibitor, and 20 μl of the eluate were directly applied to the gel. Another portion of 20 μl of the eluate was treated with RNAse A (40 ng/μl) together with 9 U BamHI for 1 h at 37° C. in a reaction volume of 25 μl and then applied to the gel.

A marker lane contains 1 μg MMW DNA.

The results show that the diatomaceous earth suspensions have NA binding properties similar to SC. Both dsDNA (component I molecules) and ssRNA (23S and 16S rRNAs) were bound. Plasmid DNA was sufficiently pure to be completely linearized (component III) by BamHI.

EXAMPLE F2

NA purification from gram-negative bacteria

9 Different species of gram negative bacteria known to cause disease in humans were cultured on solid agar plates. Of each of these bacterial species 5 to 10 μl was scraped off the plates and used as input material for NA extractions according to protocol Y, and 40 μl SC or 40 μl of the Celite 521 suspension were used as NA carrier.

The extractions in which SC was used had to be stopped during the first wash since the NA silica complexes could no longer be homogenized, not even after vortexing for a long time (over 3 min.). On the other hand, extractions in which Celite 521 was used proceeded without problems, presumably due to the larger particle sizes of the diatomaceous earth relative to the SC particles. The NA was eluted with 70 μl TE buffer without RNAsin and part of the eluate (20 μl) was electrophoresed through a 1% agarose gel.

The marker lanes contain 1 μg MMW DNA. Results for the following types of bacteria were obtained:
1: *Campylobacter pylori*
2: *Yersinia enterolvtica* type 3
3: *Neisseria meninoitidis*
4: *Neisseria gonorrhoeae*
5: *Haemoohilus influenzae* type b
6: *Kelbsiella pneumoniae*
7: *Salmonella typhimurium*
8: *pseudomonas aeruginosa*
9: *Escherichia coli* K1-083

HMW bacterial DNA and rRNAs could be detected using this procedure.

DNA/RNA purification of Escherichia coli JM101

SECTION G

DNA/RNA purification of Escherichia coli JM101

Isolation of NA from gram negative bacteria is possible according to this invention. In bacterial cells high levels of high molecular weight DNA (HMW DNA) and ribosomal RNA are present. Example G1 shows that NA can be purified from bacterial cells using various chaotropic substances with silica as NA binding solid phase.

EXAMPLE G1

NA isolation/purification (endogeneous) from bacterial cells with various chaotropic substances and silica as NA binding solid phase NA was isolated from 50 μl overnight bacterial e culture JM101 in presence of 900 μl chaotropic substance and 40 μl SiO$_2$. The high level of HMW-DNA and endogeneous ribosomal RNA (16S and 23S) allows detection of isolated NA by UV illumination of ethidium bromide stained gels. Isolations were carried out according to protocol Y*, and 25% of the eluted NA (40 μl portions) was analysed on agarose gel.

TABLE G1

Relative efficiency of HMW DNA and rRNA isolation from bacterial cell samples using various chaotropic substances in combination with silica

| Sample nr. | chaotropic substance used | relative efficiency of HMW-DNA recovery | relative efficiency of rRNA recovery |
|---|---|---|---|
| 1 | 3M KI | 1 | >1 |
| 2 | 3M NaI | 1 | 1 |
| 3 | 3M NaSCN | 1 | 1 |

Legend

Table G1 summarizes the results of the agarose gel analysis. Quantification of HMW-DNA and rRNA recovery has been compared with the procedure where GuSCN was used as chaotropic substance in combination with silica: 1 in table G1 indicates equally efficient DNA or RNA recovery. >1 in table G1 indicates better recovery.

The *E.Coli* rRNA marker (Boehringer) was taken as a reference for isolation endogeneous RNA from bacterial cells.

SECTION H

DNA purification with alternative solid phase capable to bind NA and quanidiniumthiocyanate as chaotropic substance.

To show that NA isolation/purification can be performed with GuSCN and several silica derivates or latexparticles (see material & methods) pure plasmid was added in a low salt buffer (Tris 10 mM-EDTA 1 mM pH 8.0) and then isolated according to protocol Y, however steps 7 and 9 were omitted (elution with TE was not carried out). The silica/latex particles with bound NA were brought in the PCR reaction mixture. The isolated DNA can be detected by the PCR-method. Example H1 shows that NA can be purified using alternative solid phases in combination with GuSCN as chaotropic substance and detection by the PCR method.

EXAMPLE H1

DNA purification with alternative solid phases and GuSCN 0.5 μg pGem3p24 present in 50 μl Tris 10 mM/EDTA 1 mM pH 8.0 was mixed with 80 μl silica suspension or 80 μl latex suspension (see Materials & Methods) and 900 μl lysis buffer L6.

After washing and drying at 56° C. according to protocol Y (no elution step) the pellet was resuspended in 50 μl water. A 20 μl portion of the plasmid-silica suspension was used in the PCR-mixture in presence of HIV specific primers (Material & Methods), 5 μl of 10×concentrated PCR-buffer, 1 μl 10 mM dNTPs, 2 Units Tao DNA polymerase and water to a final volume of 50 μl were added and the amplification reaction was started (1 cycle comprised 1 min. at 95° C.; 1 min. at 37° C. and 3 min. at 72° C.).

10 μl aliquots were taken from the reaction mixtures after 30 cycles and analysed on a 2% agarose gel. Isolation of NA with the latex particles did not obtain pellets like isolation of NA with silica.

When 1 ml washing liquid L2 was mixed with 300 μl 70% EtOH a latex containing band was found between two liquid phases. The latex particles are detectable by their colour. The latex containing fraction isolated was washed twice with 70% EtOH and after centrifugation formed a small pellet in the Eppendorff tube.

TABLE H1

Detection of DNA isolated using alternative solid phases in combination with quanidinium thiocyanate as chaotropic substance, using PCR amplification and gel analysis for detection.

| sample nr. | NA solid phases | Detected level of HIV p24 DNA after amplification (LMW DNA) |
|---|---|---|
| 1 | Silica Coarse (control) | + + |
| 2 | 12 MAAM - C2 | + |
| 3 | 12 MAAM - C3 | + |
| 4 | 12 MAAM - C4 | + |
| 5 | 12 MAAM - C6 | + + |
| 6 | 12 MAAM - C8 | + |
| 7 | 12 MAAM - C10 | + |
| 8 | 12 MAAM - C18 | + + |
| 9 | VQ 69 (Hydrophobic) | + + |
| 10 | VQ 58B (Hydrophobic) | + + |
| 11 | AGY 1515 (Hydrophilic) | + |
| 12 | AGF 27G (Hydrophilic) | + |
| 13 | ACN3red (Hydrophilic) | + |

Legend

The results are summerized in table H1. The expected 290bp HIV amplimer fragment was observed in all cases after 30 cycles. The size of the fragments was compared with marker φx 174 RF DNA Hae III digest (Pharmacia) also loaded on the gel.

+ + : indicates the detection of the HIV specific 290 bp fragment on the agarose gel at an equal level as using Silica Coarse as solid phase (control).

+ :indicates a detectable level of the 290 bp fragment, lower than the control Silica Coarse.

SECTION I

Purification with NA-binding filters and GuSCN

NA-binding filters (see Materials & Methods) can replace the SiO2 in the isolation of nucleic acid according to protocol Y**.

Although normally no release of DNA takes place in the low salt buffer (Tris 10 mM-EDTA 1 mM pH 8.0) this optional problem is set aside by inserting the filter with DNA bound to it in the PCR-reaction mixture instead of eluting the DNA from the filter. Example I1 shows that purification of NA can be performed with a NA-binding filters and GuSCN as a chaotropic substance analysed by the PCR-method.

EXAMPLE I1

DNA isolation/purification with a DNA-binding filter and detection by the PCR-amplification Pure pGem3p24 DNA (concentration 1 μg; 0,01 μg and 0,005 μg) in 50 μl Tris 10mM/EDTA 1 mM pH 8.0 was added to three DNA-binding filters, (PVDF, Hybond N and Nitrocellulose) with a size of 1 cm×1 cm and 900 μl GuSCN (lysisbuffer L6).

After washing (no centrifugation steps) and drying at 56° C. (according to protocol Y**) the filter with DNA bound to it was brought directly in the PCR-mixture. In presence of HIv specific primers amplification was performed in the PCR-cycler.

The reaction mixture futher consists of 5 μl 10×concentrated PCR-buffer, 1 μl 10mM dNTPs, 2 units Taq DNA polymerase and water to a final volume of 50 μl. Subsequently the amplificaton reaction was started.

10 μl aliquots were taken from the raction mixtures after 30 cycles (see example H1) and analysed on a 2% agarose gel.

TABLE I1

Detection of DNA isolated using filters as alternative NA binding solid phase in combination with GuSCN as chaotropic substance using PCR-amplification and gel analysis for detection.

| sample nr. | NA binding solid phase | Amount of input DNA | Amount of HIVp24 DNA after amplification |
|---|---|---|---|
| 1 | Hybond N | 1.0 μg | + |
| 2 | Hybond N | 0.01 μg | o |
| 3 | Hybond N | 0.005 μg | o |
| 4 | Nitrocellulose | 1.0 μg | + |
| 5 | Nitrocellulose | 0.01 μg | o |
| 6 | Nitrocellulose | 0.005 μg | o |
| 7 | PVDF-millipore | 1.0 μg | + + |
| 8 | PVDF-millipore | 0.0 μg | + |
| 9 | PVDF-millipore | 0.005 μg | + |

The result summarized in Table I1. The expected 290 by HIV amplimer fragment was observed. The fragment was compared with a commercial φxHaeII + + :strong Ethidium bromide stained 290 bp fragment detectable on agarose gel + :detectable 290 bp fragment o :290 gp fragment not detected For comparison: 7ng of purified pGem3p24 DNA added to the PCR amplification mixture gives a 290 bp fragment quantified as + +

We claim:

1. A process for isolating nucleic acid from a nucleic acid-containing starting material comprising mixing the starting material, a chaotropic substance and a nucleic acid binding solid phase, separating the solid phase with the nucleic acid bound thereto from the liquid, and washing the solid phase nucleic acid complexes.

2. A process according to claim 1, wherein the starting material employed is a nucleic acid-containing biological material.

3. A process according to claim 1, wherein the chaotropic substance is at least one compound selected from the group consisting of a guanidinium salt, sodium iodide, potassium iodide, sodium thiocyanate and urea.

4. A process according to claim 3, wherein the guanidinium salt employed is guanidinium (iso)thiocyanate.

5. A process according to claim 1, wherein the nucleic acid binding solid phase is selected from the group consisting of silica particles, cuvettes, microtiter plates, filter membranes, polystyrene beads and nitrocellulose paper.

6. A process according to claim 1 for isolating DNA or RNA.

7. A process according to claim 1, wherein the solid phase comprises silica particles having a particle size ranging substantially between 0.05 and 500 μm.

8. A process according to claim 1, wherein the solid phase comprises silica particles having a particle size ranging substantially between 0.1 and 200 μm.

9. A process according to claim 1, wherein the solid phase comprises silica particles having a particle size ranging substantially between 1 and 200 μm.

10. A process according to claim 1, wherein the solid phase-nucleic acid complexes are separated from the liquid by sedimentation and wherein the complexes are washed with a chaotropic substance-containing washing buffer.

11. A process according to claim 10, wherein the solid phase-nucleic acid complexes washed with washing buffer are further washed successively with one or more alcohol-water solutions and then dried.

12. A process according to claim 11, wherein the nucleic acid present in the washed and dried solid phase-nucleic acid complexes is eluted by means of an aqueous buffer suitable for eluting nucleic acid.

13. A process to amplify captured nucleic acids comprising mixing the starting material, a chaotropic substance and a nucleic acid binding solid phase, separating the solid phase with the nucleic acid bound thereto from the liquid, washing the solid phase nucleic acid complexes and contacting the solid phase-nucleic acid complexes with a mixture comprising components that amplify the nucleic acid.

14. A test kit for carrying out the process according to claim 13 comprising components to amplify nucleic acid.

* * * * *